(12) United States Patent
Casey, II et al.

(10) Patent No.: US 7,556,643 B2
(45) Date of Patent: Jul. 7, 2009

(54) GRAFT INSIDE STENT

(75) Inventors: Thomas V. Casey, II, Grafton, MA (US); Kristoff Nelson, Boston, MA (US); Fergus Quigley, Watertown, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/202,542

(22) Filed: Jul. 24, 2002

(65) Prior Publication Data

US 2004/0019373 A1 Jan. 29, 2004

(51) Int. Cl.
*A61F 2/06* (2006.01)

(52) U.S. Cl. .................................. 623/1.13; 623/1.15

(58) Field of Classification Search ................ 623/1.13, 623/1.18, 1.2, 1.32, 1.49, 1.24, 1.25
See application file for complete search history.

(56) References Cited

U.S. PATENT DOCUMENTS

| | | | |
|---|---|---|---|
| 5,122,154 A | 6/1992 | Rhodes | |
| 5,219,355 A | 6/1993 | Parody et al. | |
| 5,360,443 A | 11/1994 | Barone et al. | |
| 5,571,173 A | 11/1996 | Parodi | |
| 5,578,071 A | 11/1996 | Parodi | |
| 5,578,072 A | 11/1996 | Barone et al. | |
| 5,643,208 A | 7/1997 | Parodi | |
| 5,674,241 A * | 10/1997 | Bley et al. | 623/1.2 |
| 5,797,949 A | 8/1998 | Parodi | |
| 5,891,193 A * | 4/1999 | Robinson et al. | 128/898 |
| 5,954,764 A | 9/1999 | Parodi | |
| 6,123,723 A | 9/2000 | Konya | |
| 6,124,523 A * | 9/2000 | Banas et al. | 623/1.15 |
| 6,156,064 A | 12/2000 | Chouinard | |
| 6,224,625 B1 | 5/2001 | Jayaraman | |
| 6,238,432 B1 | 5/2001 | Parodi | |
| 6,245,102 B1 * | 6/2001 | Jayaraman | 623/1.15 |
| 6,254,642 B1 * | 7/2001 | Taylor | 623/23.64 |
| 6,325,820 B1 * | 12/2001 | Khosravi et al. | 623/1.13 |
| 6,451,047 B2 * | 9/2002 | McCrea et al. | 623/1.13 |
| 6,517,570 B1 * | 2/2003 | Lau et al. | 623/1.13 |
| 7,226,474 B2 * | 6/2007 | Iancea et al. | 623/1.13 |

FOREIGN PATENT DOCUMENTS

| | | |
|---|---|---|
| GB | 2347861 A | 9/2000 |
| WO | WO 02/24247 A1 | 3/2002 |

\* cited by examiner

*Primary Examiner*—Corrine M McDermott
*Assistant Examiner*—Christopher D Prone
(74) *Attorney, Agent, or Firm*—Vidas, Arrett & Steinkraus

(57) ABSTRACT

An endoluminal self-expanding prosthesis for placement in a blood vessel, duct or lumen, to hold it open. The prosthesis includes a stent with a graft extending within the stent. The stent is an elongated self-expanding stent with an open tubular wall structure. The graft is an elongated compressible generally tubular graft. One end of the graft is secured to the inside of the stent and the graft extends therethrough. The stent is deployed allowing the free flow of blood through the open-celled structure, and the graft is freely deployed secondarily within the stent by the blood flowing therethrough. The present invention is not subject to significant distal migration during delivery and placement of the prosthesis.

25 Claims, 6 Drawing Sheets

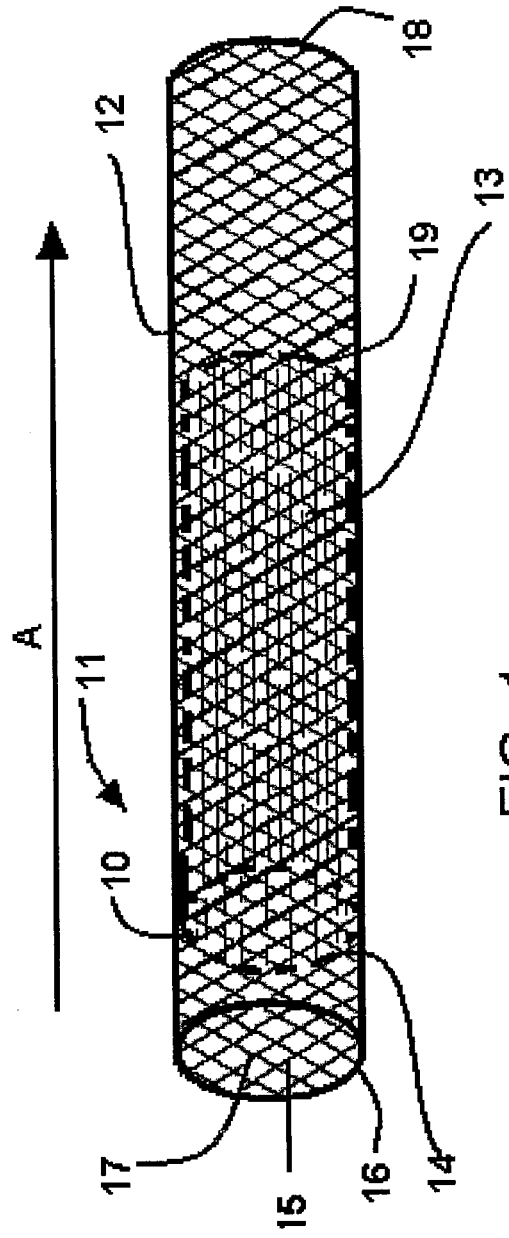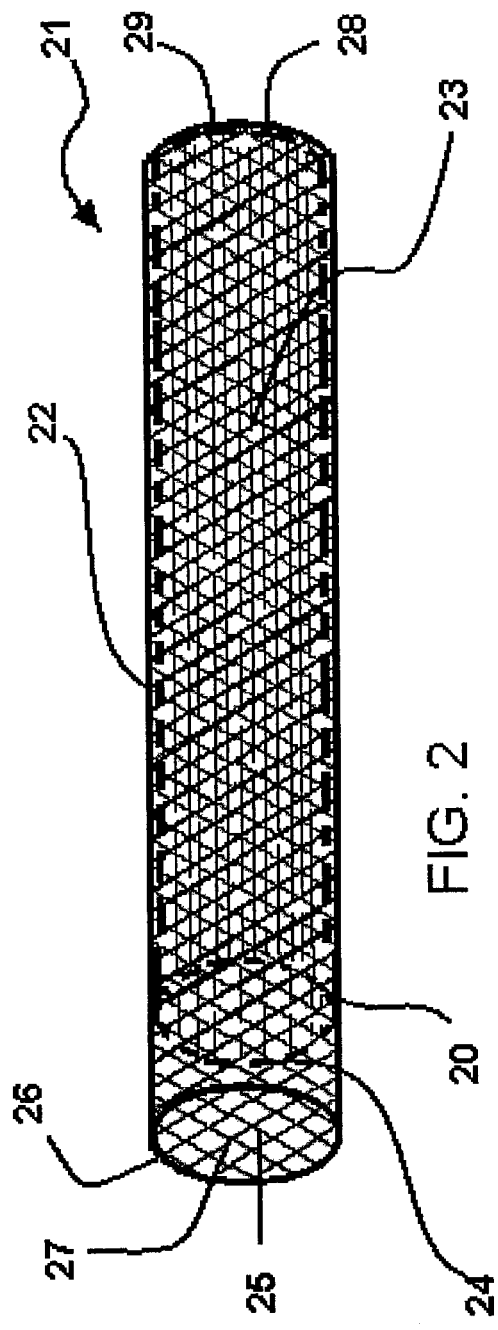

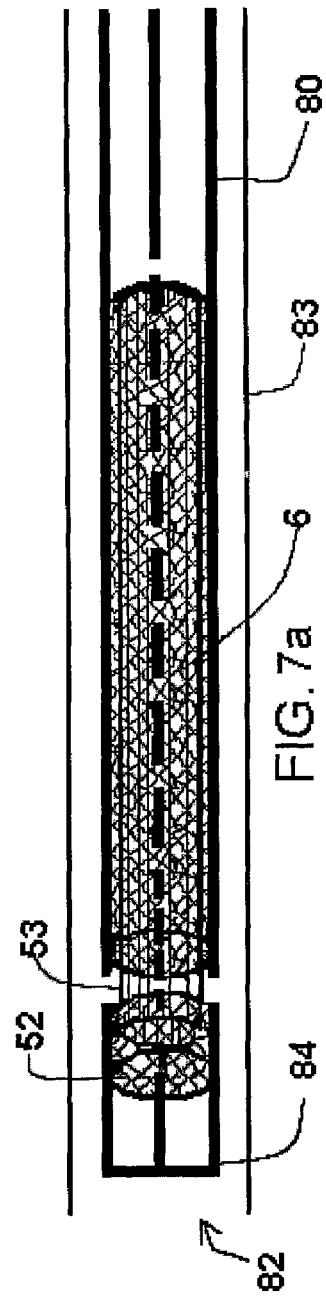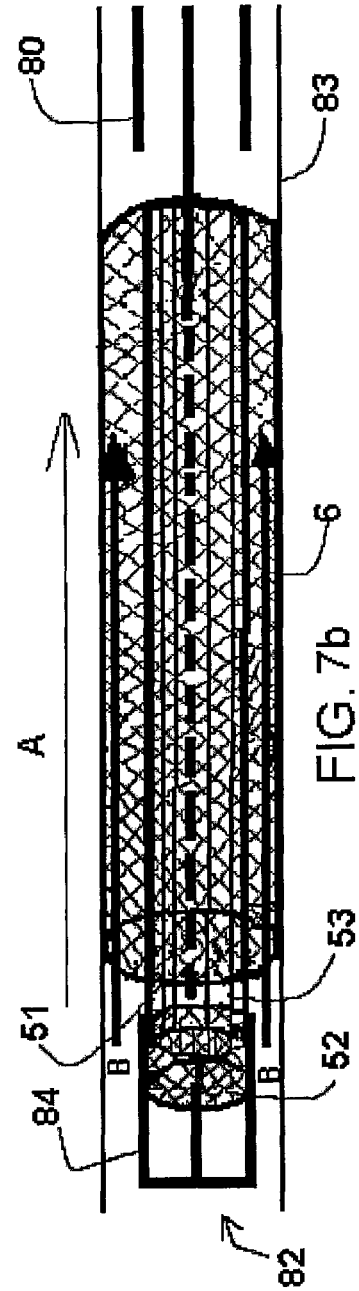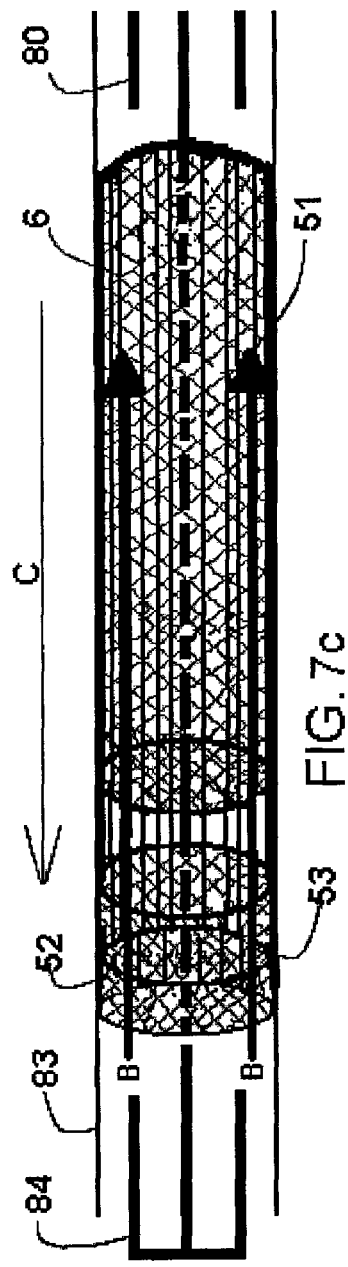

GRAFT INSIDE STENT

FIELD OF THE INVENTION

The present invention relates generally to a system and method of delivering an endoluminal prosthesis within a body lumen. More particularly, the present invention provides a delivery device retaining an endoluminal prosthesis during delivery and additionally for the deployment of the endoluminal prosthesis at a target site within the lumen.

BACKGROUND OF THE INVENTION

Endoluminal prostheses are typically used to repair, replace, or otherwise correct a diseased or damaged blood vessel. An artery or vein may be diseased in a variety of ways. The prosthesis may therefore be used to prevent or treat a wide variety of defects such as stenosis of the vessel, thrombosis, occlusion, or an aneurysm and dissections.

One type of endoluminal prosthesis used in treatment and repair of diseases in various blood vessels is a stent. A stent is a generally longitudinal tubular device which is useful in open and support various lumens in the body. For example, stents may be used in the vascular system, urogenital tract and bile duct, as well as in a variety of other applications in the body. Endovascular stents have become widely used for the treatment of stenosis, strictures, and aneurysms in various blood vessels. These devices are implanted within the vessel to open and/or reinforce collapsing or partially occluded sections of the vessel.

Stents are generally open ended and are radially expandable between a generally unexpanded insertion diameter and an expanded implantation diameter which is greater than the unexpanded insertion diameter. Stents are often flexible in configuration, which allows them to be inserted through and conform to tortuous pathways in the blood vessel. The stent is generally inserted in a radially compressed state and expanded either through a self-expanding mechanism, or through the use of balloon catheters.

A graft is another type of endoluminal prosthesis which is used to repair and replace various body vessels. Whereas a stent provides structural support to hold a damaged vessel open, a graft provides an artificial lumen through which blood may flow. Grafts are tubular devices which may be formed of a variety of materials, including textile and non-textile materials natural and synthetic. Grafts also generally have an unexpanded insertion diameter and an expanded implantation diameter which is greater than the unexpanded diameter. The graft is sutured to the lumen to secure it in place.

It is also known to use both a stent and a graft to provide additional support for blood flow through weakened sections of a blood vessel. In endovascular applications the use of a stent and a graft is becoming increasingly important because the combination not only effectively allows the passage of blood therethrough, but also ensures the implant will remain open and provides containment of the blood. Sealing significantly reduces the transmission of arterial pressure through to the diseased segment.

The use of both a stent and a graft is available in various forms. One such form is a stent-graft composite where the stent is cast onto or imbedded into a graft, leaving the graft inseparable from the stent, as described in U.S. Pat. No. 6,156,064 to Chouinard. Another stent-graft form is a multi-stage stent graft, such as those described in U.S. Pat. No. 5,122,154 to Rhodes, and U.S. Pat. No. 5,578,071 to Parodi. A graft and the stent can be attached or unattached to each other. The graft is anchored/fixed to the vascular wall by the deployment of a stent inside the graft (endoskeletal) which sandwiches the graft between the vascular wall and the stent.

The deployment of multi-stage stent graft is complex because of the different expansion properties between the graft and the stent, and the frictional relationship between the two in the delivery sheath. As the stent expands within the graft, irregular expansion of the graft may occur, provoking graft deformities, such as creases or folds, on the graft that act as constrictor rings to limit the expansion of the stent.

The micro motion of the stent expanding inside the graft can produce distal migration of the graft material. An obstruction of blood flow is experienced when the stent covered graft is initially deployed. Deployment of the stent-graft is not instantaneous, rather, it is deployed in a piece by piece manner. As the stent-graft begins to expand from its proximal target zone, it naturally "flows open" and thus is subject to the arterial pulsatile flow. The blood cannot flow through the graft, creating retrograde pressure. The retrograde pressure, caused by the obstruction of blood flow, causes the graft to twist, crumble and not properly unfold, and the stent may not anchor properly, move or shift during or after deployment. Primarily, the arterial pulsatile flow acts upon the stent-graft, and if sufficient traction has not developed between the stent-graft and vessel, causes detrimental distal movement. Importantly, this affects the proximal deploy/placement accuracy.

Retrograde pressure is also experienced where the stent-graft is partially covering an outlet vessel, creating an obstruction of blood flow from the feed vessel to the outlet vessel. The blood begins to back up within the feed vessel, leading to other complications. The stent-graft cannot be repositioned, once the graft is partially or fully deployed beyond the point of being able to be repositioned, and sandwiched between the stent and the artery wall, without damaging the stent-graft or possibly injuring the artery wall.

Thus, there is a need in the art for an endoluminal prosthesis placement that eliminates such problems associated with concurrent deployment of a stent and graft, and blood flow obstruction. There is a need for an endoluminal prosthesis that is least obstructive to the blood flow upon deployment and modular assembly. The endoluminal prosthesis must also allow for selective cellular ingrowth, provide reliable prosthesis fixation, long term durability and allow for post-deployment adjustments/anatomical evolution.

SUMMARY OF THE INVENTION

In accordance with the present invention, the foregoing advantages have been achieved through the endoluminal self-expanding prosthesis of the present invention.

The present invention includes an elongated self-expanding stent and an elongated compressible tubular graft/covering. The stent includes a pair of spaced apart ends and an open tubular wall structure therebetween. The tubular wall structure of the stent has an internal surface defining a stent lumen. The graft having opposed ends and a graft wall therebetween. One end of the graft being secured to the internal surface of the stent below one of the stent ends. The graft extending from the graft secured end through the stent lumen. One end of the stent remains without the graft extending through the stent lumen.

BRIEF DESCRIPTION OF THE DRAWINGS

FIG. 1 is a schematic illustration of the endoluminal self-expanding prosthesis according to the present invention having an elongate stent extending longitudinally beyond a graft.

FIG. 2 is a schematic illustration of the endoluminal self-expanding prosthesis according to the present invention having an elongate stent extending co-longitudinally with a graft.

FIGS. 7a, 7b and 7bc are schematic illustrations of the deployment device of FIG. 5, having a proximal sheath deploying the endoluminal self-expanding prosthesis and a distal sheath deploying the supporting stent of the present invention.

DETAILED DESCRIPTION

Figure 3:
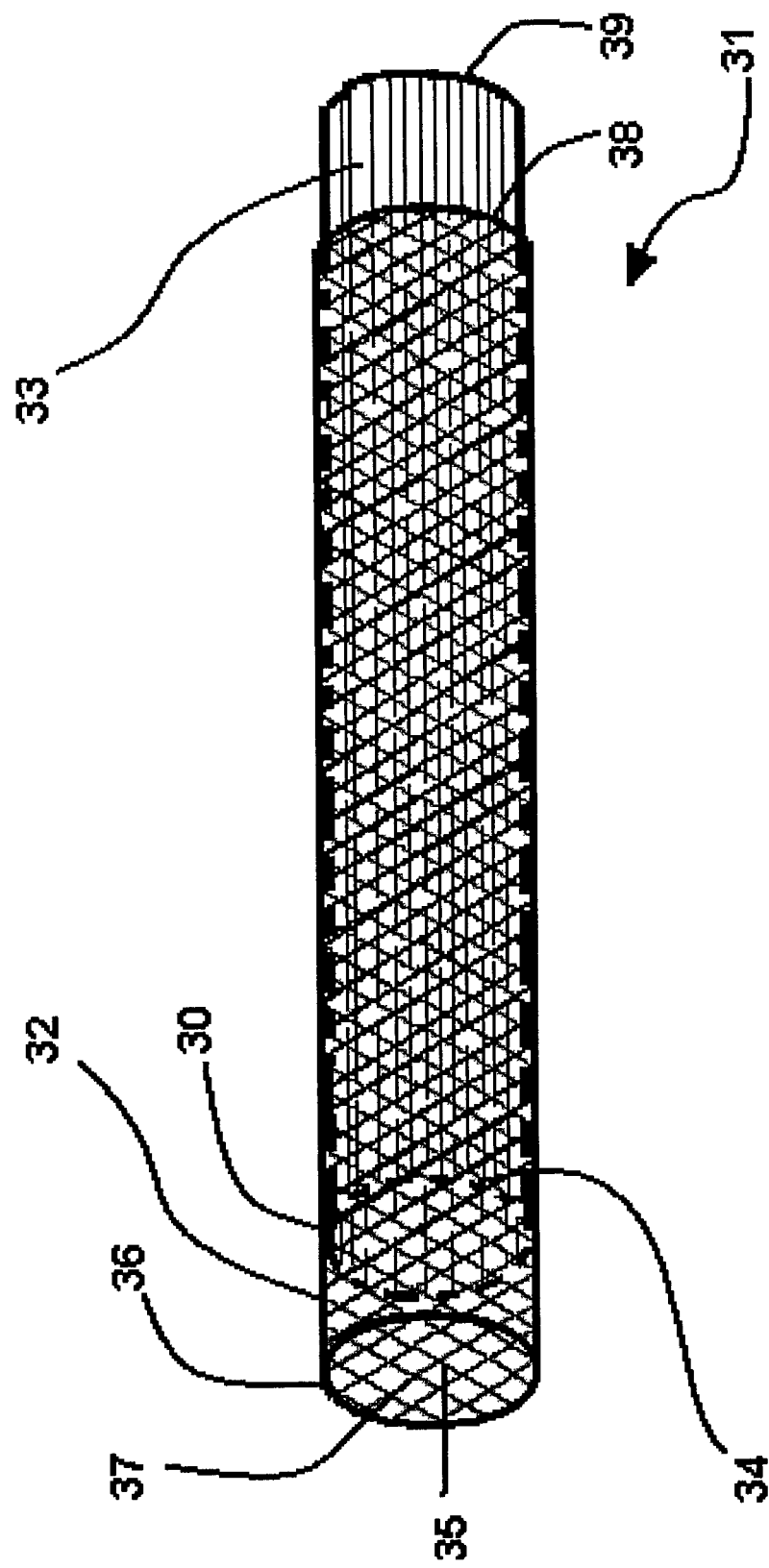
FIG. 3 is a schematic illustration of the endoluminal self-expanding prosthesis according to the present invention having an elongate graft extending longitudinally beyond the stent.

The present invention relates to a graft-inside-stent prosthesis, as shown in FIGS. 1-5, for intraluminal delivery. The prosthesis is particularly suited for use as a vascular graft. The prosthesis of the present invention includes a graft attached to and at least partially covered by a stent.

The present invention addresses the problems associated with prior art stent-graft endoprosthesis, such as graft deformities like creases, folds, and distal migration during stent deployment.

In the present invention the stent is located exterior to the graft, exo-skeletal between the graft and the aortic wall. Therefore, unlike prostheses of the prior art, the graft is not sandwiched in place between the stent and the vessel, for example, the aorta. Instead, in the present invention the graft freely deploys secondarily to the stent within the stent by the blood flowing therethrough.

Moreover, the prosthesis of the present invention employs an open-celled or porous stent which is in direct contact with the aortic wall. This permits ingrowth of cells for the stabilization of implanted endoprosthesis, and superior device fixation. The graft itself is generally impermeable inhibiting substantial leakage of blood therethrough.

Generally, the design of the present invention includes a graft attached to the inner surface of the stent. In the desired design the graft is attached below the upstream end of the stent leaving upstream ends without a graft covering defining a bare segment. This provides for uninterrupted blood flow through the expanded open-cell stent as initial deployment and positioning take place. It provides for placement of the bare segment across a patency vessel (e.g., renal left subclavan). As the remainder of the prosthesis is deployed, the graft is freely expanded by the blood flowing therethrough. Furthermore, the stent extending upstream from the graft is desired when anchoring the stent para-subclusion or para left common carotid or other artery The open-celled or porous, extending section of the stent may cover the outlet arteries without disturbing the blood flow from the aorta into the outlet arteries. The simplicity of the present invention permits the introduction of the prosthesis into the lumen and the deployment by a reduced profile delivery system. The prosthesis itself provides minimal obstruction of the blood flow and minimizes associated retrograde pressure problems.

The attachment of the graft to the stent may be at one end of the stent or anywhere between the two ends of the stent. The attachment of the graft to the stent may be accomplished by mechanically securing or bonding/fixing the graft and the stent to one and the other. Mechanical securement includes, but is not limited to, the use of sutures, anchoring barbs, textile cuffs, ePTFE cuffs, and the like. Bonding includes, but is not limited to, chemical bonding, for instance, adhesive bonding, thermal bonding and lamination, fusing and the like.

Stent

As is known in the art, the stent has two diameters, the compressed diameter and the expanded diameter wherein the compressed diameter is substantially smaller than the expanded diameter. The compressed diameter of the stent varies depending on the materials of construction and structure of the stent. In general, the compressed diameter must be small enough to allow for implantation through the vasculature via a minimally invasive deployment system (not shown). The expanded diameter needs to be substantially the same diameter as the vasculature in which it is to replace or repair. The expanded diameter needs to be large enough allow to the stent to sufficiently secure to the aortic wall without acting as a driving force to expand or dilate the vessel.

Various stent types and stent constructions may be employed in the invention. The stents may be capable of radially contracting, as well, and in this sense can best be described as radially distensible, deformable or conformable. Self-expanding stents include those that have a spring-like action which causes the stent to radially expand, or stents which expand due to the pre-set memory properties of the stent material for a particular configuration at a certain temperature range. Nitinol is one material which has the ability to perform well while both in spring-like elastic mode, as well as in a memory mode based on temperature. Other materials are of course contemplated, such as stainless steel, platinum, gold, titanium and other bicompatible metals, as well as polymeric based stents, or indeed composites of the aforementioned.

The configuration of the stent may also be chosen from a host of geometries. For example, wire stents can be fastened into a continuous helical pattern, with or without a wavelike or zig-zag in the wire, to form a radially deformable stent. Individual rings or circular members can be linked together such as by struts, sutures, welding or interlacing or locking of the rings to form a tubular stent structure. Tubular stents useful in the present invention also include those formed by etching or cutting a pattern from a tube. Such stents are often referred to as slotted stents. Furthermore, stents may be formed by etching a pattern into a material or mold and depositing stent material in the pattern, such as by chemical vapor deposition or the like.

Graft

Any known graft material and structure may be used to form the graft of the present invention. The graft preferably has generally a tubular configuration. The graft may be made from a variety of well known materials, provided they have the requisite strength characteristics and biocompatibility properties. Examples of such materials are polyester, polypropylene, polyethylene, polytetrafluoroethylene, expanded polytetrafluoroethylene and polyurethane, DACRON, TEFLON (polytetrafluoroethylene), and TEFLON coated DACRON as well as composites of the aforementioned. The material can be extruded, knitted or woven, and can be warp or weft knitted. The graft can also be coated or impregnated with a bio-erodible, or degradable material, such as albumin, collagen, heparin or similar coating material. Additionally, the graft could have a coating of a biologically inert material, such as TEFLON or porous polyurethane.

In general, the diameter of the graft varies depending on the use but generally should be substantially the same diameter as the inside diameter of the stent or vessel in which it is to replace, repair or augment. The diameter should be large enough to allow for unobstructed blood flow and prevent retrograde pressure build-up in the blood flow while maintaining sufficient traction for long-term fixation. While cylindrical tubular configurations are shown, other tubular configurations may be employed.

One embodiment of the present invention is a prosthesis 11 as shown in FIG. 1. The prosthesis 11 is a generally tubular structure which includes a stent 12 and a graft 13. The stent 12 is an elongated self-expanding stent of the type described above. The stent 12 has a pair of spaced apart ends, an upstream end 16 and a downstream end 18 and an open tubular wall structure therebetween. The tubular wall structure has an external surface and an internal surface which defines the stent lumen 15. The direction of blood flow from the upstream end to the downstream end is indicated by arrow A.

The graft 13 is an elongated compressible generally tubular graft of the type described above. The graft 13 has opposing ends, a secured end 10 and unattached end 19, and a graft wall therebetween. The graft secured end 13 is secured to the internal surface of the stent 12 defining the point of attachment 14 on the stent. The graft 13 can be attached at the upstream end 16 of the stent or anywhere inbetween the stent ends. The graft 13 extends from the graft secured end 10 co-longitudinally through the stent lumen 15. A portion of the stent from the upstream end 16 of the stent to the point of attachment 14 defines the extending section 17 of the stent. The extending section 17 of the stent remains without the graft 13 within its lumen.

As shown in FIG. 1, the stent 12 longitudinally extends beyond the graft 13. The stent downstream end 18 longitudinally extends beyond the graft's unattached end 19. Therefore the unattached end 19 of the graft is within the stent lumen 15, and circumferentially surrounded by the stent 12.

Another embodiment of the present invention, as shown in FIG. 2, includes a prosthesis 21 which has similar components as prosthesis 11 in FIG. 1. The graft 23 is secured to the interior surface of the stent 22. A portion of the stent 22 from the upstream end 26 to the point of attachment 24 remains without the graft 23 within the lumen 15 defined as the extending section 27. The graft 23 longitudinally extends within the stent lumen 25. The stent's downstream end 28 and the graft's unattached end 29 are substantially longitudinally coextensive.

In yet another embodiment of the present invention as shown in FIG. 3, prosthesis 31 has similar components as the prosthesis 21 in FIG. 2. Graft 33 is secured to the stent 32 between the upstream end 36 and downstream end 38 of the stent 32. The graft 33 extends co-longitudinally within the stent lumen 35 and longitudinally protrudes beyond the downstream end of the stent 38. The unattached end of the graft 39 extends longitudinally beyond the downstream stent end 38. The graft 33 is secured to the stent at attachment location 34 inwardly of upstream end 36 of stent 32.

Figure 4:
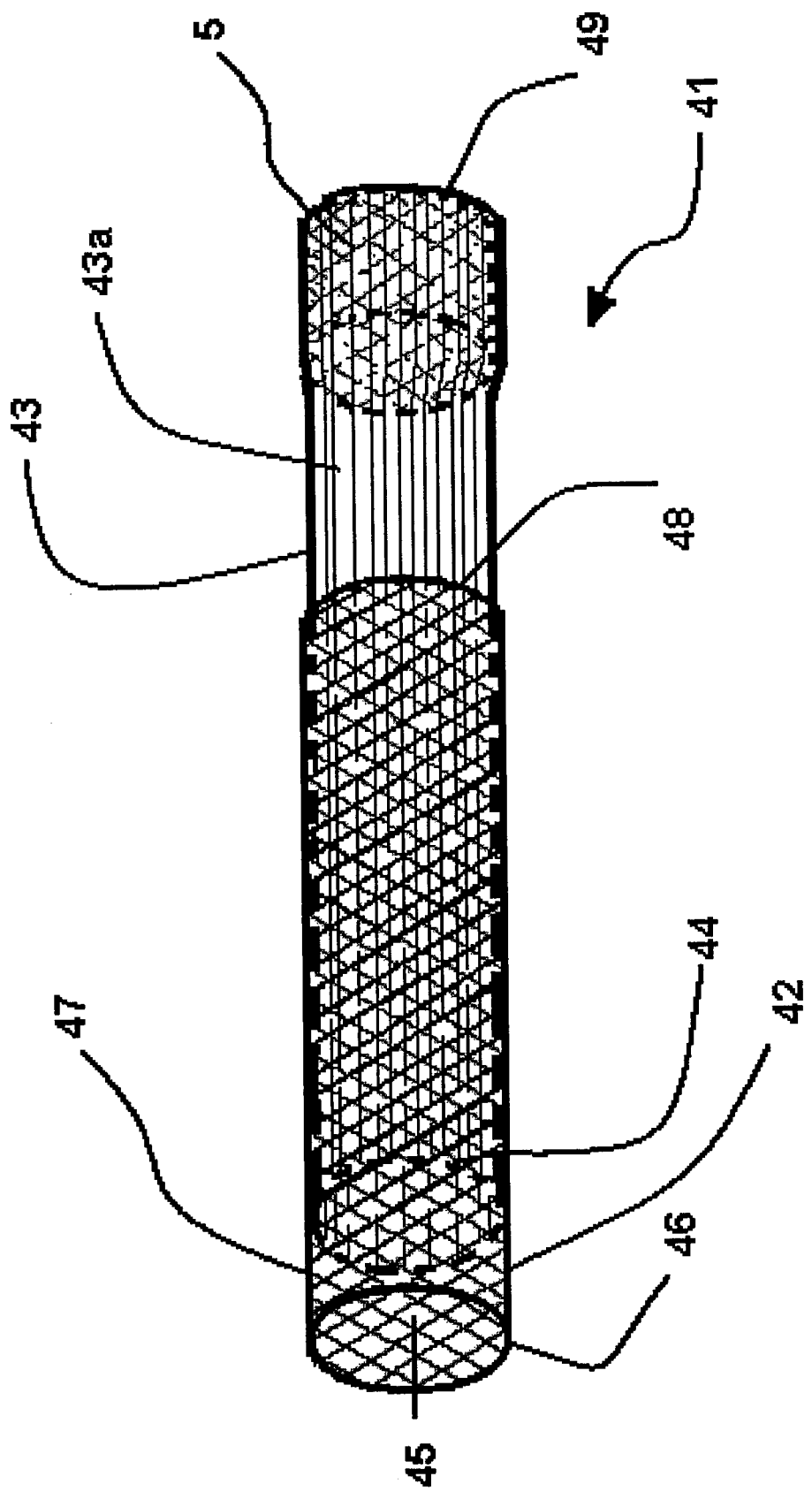
FIG. 4 is a schematic illustration of the endoluminal self-expanding prosthesis according to the present invention having a supporting stent within an end of the graft.

In a further embodiment, as shown in FIG. 4, prosthesis 41 is similar to prosthesis 31 of FIG. 3 with an additional supporting stent for securing the grafts' unattached end 49. Graft 43 is secured to the interior surface of the stent 42 between the upstream end 46 and the downstream end 48 at location 44, so as to define a stent extending section 47. The graft 43 co-longitudinally extends within the stent lumen 45, and protrudes beyond the downstream end 48 of the stent. A supporting stent 5 may be positioned within the protruding end section 43a of graft 43. The supporting stent 5 is an elongated generally tubular stent, which may be self-expanding or balloon-expandable, of the type generally described above. The supporting stent 5 is placed within the graft 43 such that the end section 43a of the graft 43 circumferentially surrounds a portion of the supporting stent 5. The supporting stent 5 is placed within the graft 43 such that the stent 42 and the supporting stent 5 do not overlap.

Figure 5:
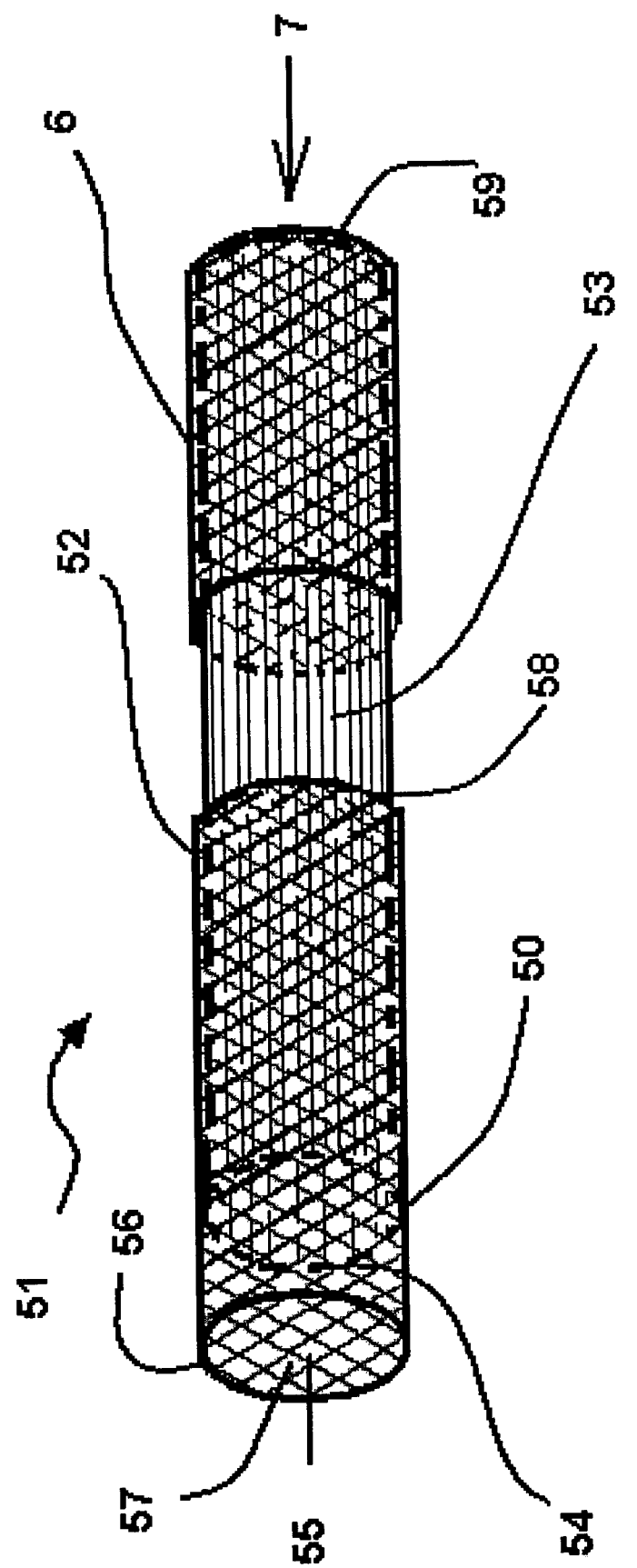
FIG. 5 is a schematic illustration of the endoluminal self-expanding prosthesis according to the present invention having a supporting stent covering a portion of the graft.

FIG. 5 shows yet a further embodiment similar to the prosthesis 41 of FIG. 4. Prosthesis 51 further includes a supporting stent 6 for additionally supporting the aortic wall. Graft 53 is secured to the interior surface of the stent 52 at attachment location 50, and co-longitudinally extends through the stent lumen 55. An extending unattached end 59 of the graft longitudinally extends beyond the downstream end 58 of the stent 52. The upstream end 56 of the stent 52 to the point of graft attachment 54 defines the extending stent section 57. The supporting stent 6 is an elongated generally tubular stent as those described above. The supporting stent 6 has two opposed ends, and an open tubular wall structure therebetween. The tubular wall structure has an internal surface defining the supporting stent lumen 7. The supporting stent 6 extends circumferentially around extending end 59, so that the end 59 is surrounded by stent 6. The supporting stent may be self-expanding or balloon-expandable. The graft 53 longitudinally extends through the supporting stent lumen 7.

Deployment of the Prosthesis

The prosthesis 11 as shown in FIG. 1 can be loaded into a delivery system for deployment within a body lumen. The delivery systems used are those known in the art. Typically, the delivery systems have introductory devices or sheaths in which the prosthesis is compressed therein. Once the vascular area is reached, the sheaths are removed, leaving the stent located endoluminally.

Figure 6A:
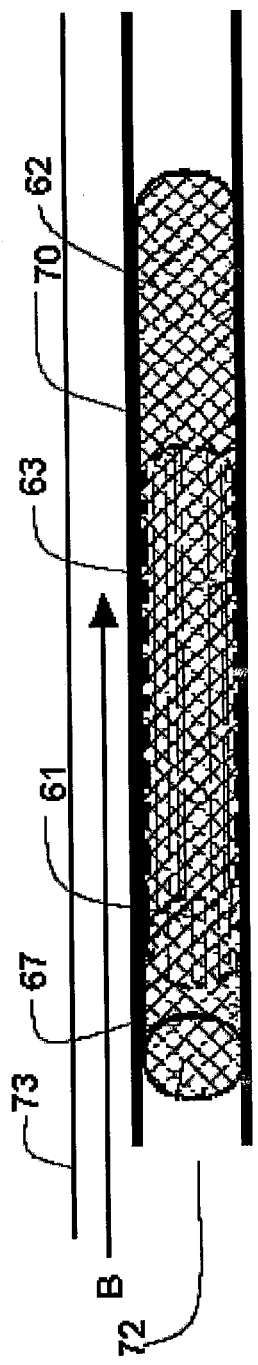
FIGS. 6a, 6b and 6c are schematic illustrations of the deployment device of FIG. 3, having outer sheath deploying the endoluminal self-expanding prosthesis of the present invention.
Figure 6B:
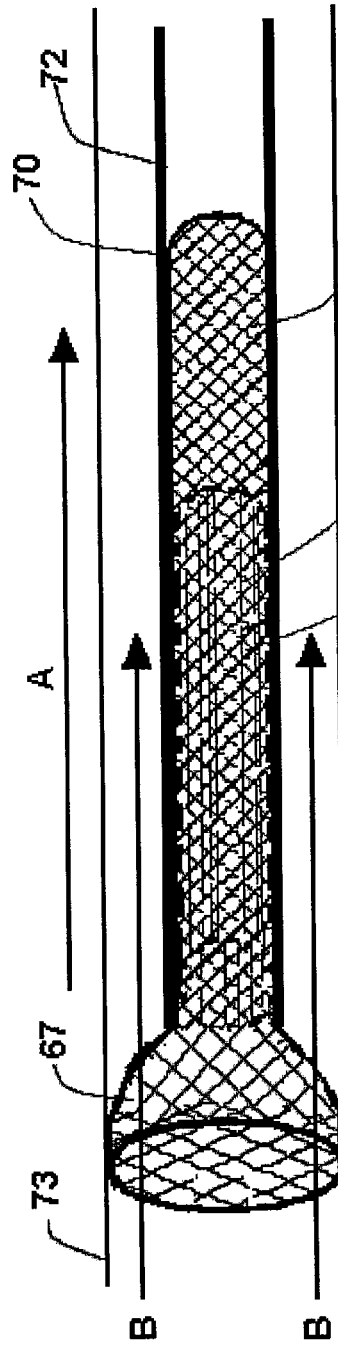
Figure 6C:
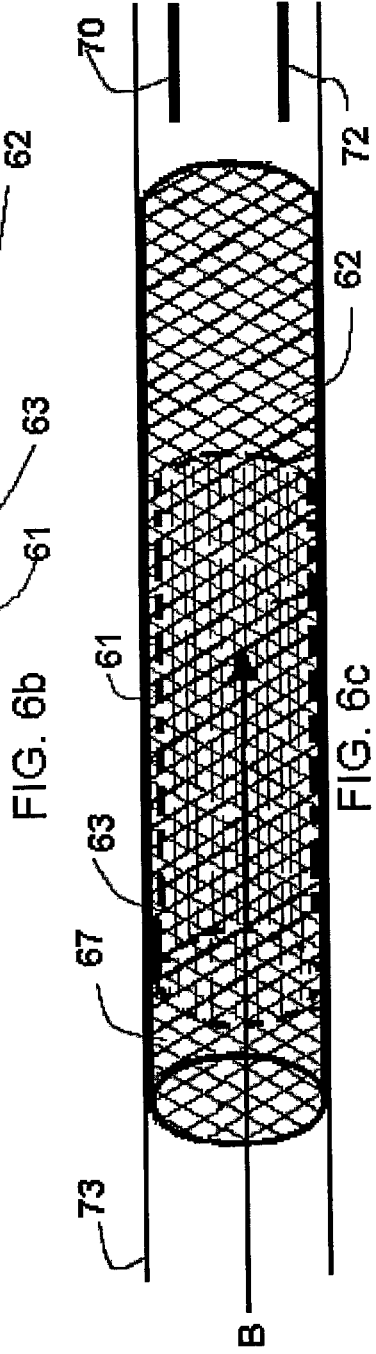

As shown in FIGS. 6a-6c, the delivery system includes an elongated outer sheath 70 which supports the prosthesis 61 in a compressed condition.

The outer sheath 70 is an elongated generally tubular structure which longitudinally surrounds the prosthesis 61. The outer sheath 70 has a diameter which is sufficiently small so as to be readily inserted within a body lumen 73 a shown in FIG. 6a.

The deployment system may further include guidewires, multiple sheaths, dilation devices, i.e. balloons, nose caps and pushers, as known in the art.

FIG. 6a shows the delivery system 72 positioned in the body lumen 73. The outer sheath 70 is retracted with respect to the prosthesis 61 in the direction of Arrow A as shown in FIG. 6b. The retraction of the outer sheath 70 progressively releases the extending end of stent 67 along its longitudinal (axial) extent and allows the extending end 67 to radially expand. The blood flow remains unobstructed as it flows through the open wall structure of the stent as depicted by Arrow B. As the outer sheath 70 further retracts the graft 63, which is positioned within the stent 62, is deployed. The graft 63 radially and longitudinally deploys by the radially expanding force of the attached stent 62, and the pressure from the blood flowing, in the direction of the Arrows B, into the graft lumen, as shown in FIG. 6c.

The prosthesis 21 as shown in FIG. 2, and the prosthesis 31 as shown in FIG. 3, are deployed using the same method as described above.

Deploying the prosthesis 41 as shown in FIG. 4 is the same process as described above followed by an additional deployment device to deploy stent 5.

The additional deployment device may be an interior sheath located within the lumen of the outer sheath as described in U.S. Pat. No. 5,954,764 to Parodi. An alternative deployment device is a separate outer sheath added to the above described delivery system as described in U.S. Pat. No. 6,123,723 to Konya. Yet another deployment device for stent 5 may include a second separate delivery system to deploy stent 42 and graft 43 are deployed first as described above. The additional deployment device for stent 5 is placed within the graft 43 lumen. Once the additional deployment device is in position the sheath is removed allowing stent 5 to radially expand. Stent 5 radially expands sandwiching the portion of the graft which is circumferentially covering stent 5.

To deploy the prosthesis 51 as shown in FIG. 5 requires an initial deployment of stent 6 prior to the deployment of stent 52 and graft 53.

As previously discussed an additional sheath or deployment device is necessary to deploy stent 6. Once the additional deployment device is in place the sheath is removed releasing stent 6. Stent 6 radially expands within the body lumen. The delivery system 72 as shown in FIG. 6a is then used to deploy the remainder of prosthesis 51. The delivery system is inserted through the lumen of stent 6. The outer sheath of the delivery system is removed, deploying stent 52 and graft 53 of FIG. 5. Graft 53 is radially and longitudinally expanded through stent 6 by the blood flow through the deployed graft 53.

As shown in FIGS. 7a-c, an additional sheath can be used within the deployment device to deliver prosthesis 51 using a single delivery system 82. FIG. 7a shows the delivery system 82 positioned in the body lumen 83. The distal sheath 80 is retracted with respect to prosthesis 51 in the direction of Arrow A as shown in FIG. 7b. The retraction of distal sheath 80 progressively releases stent 6 allowing stent 6 to radially expand. The blood flow remains unobstructed as it flows through the open wall structure of the stent as depicted by Arrow B. The proximal sheath 84 is retracted with respect to prosthesis 51 in the direction of Arrow C as shown in FIG. 7c. The retraction of proximal sheath 84 releases stent 52 and graft 53 allowing stent 52 to radially expand. Graft 53 is radially and longitudinally expanded through stent 6 by the blood flow through the deployed graft 53. While proximal sheath 84 is shown, other retaining means can be used to deploy stent 52 and graft 53 such as a nose cap, brace-like devices, or failable membranes such as a biodegradable material or bioabsorbable material which over time degrades releasing stent 52 and graft 53.

It may be appreciated that the prosthesis of the present invention provides a stent/graft composite where the stent expands to directly support an aortic wall and the graft is allowed to longitudinally expand under the pressure of the blood flow. Such an arrangement allows for unobstructed blood flow through the stent upon deployment and promotes the cellular ingrowth from direct contact of the stent to the aortic wall. Additionally, the graft is not forced in place and sandwiched between the aortic wall by the stent which promotes graft deformation.

It will be appreciated that the present invention has been described herein with reference to a certain preferred or exemplary embodiment. The preferred or exemplary embodiment described herein may be modified, changed, added to or deviated from without departing from the intent, spirit and scope of the present invention, and it is intended that all such additions, modifications, amendments and/or deviations be included within the scope of the following claims.

What is claimed is:

1. An endoluminal self-expanding prosthesis, comprising:
   an elongate self-expanding stent having a pair of spaced apart ends and an open tubular wall structure therebetween, said tubular wall structure having an internal surface defining a stent lumen; and
   an elongate compressible generally tubular graft having opposed ends and a graft wall therebetween, one end of said graft being secured to said internal surface of said stent internally of said stent ends to anchor said graft to an endoluminal wall, said graft wall extending unattached from said one end through said stent lumen to an other end of said graft, said other end of said graft being unattached, said graft being attached only at said one end.

2. A prosthesis according to claim 1 wherein the graft and the stent are substantially longitudinally coextensive.

3. A prosthesis according to claim 1 wherein the other end of said stent extends beyond the other end of said graft.

4. A prosthesis according to claim 1 wherein the other end of said graft extends beyond said other end of said stent.

5. A prosthesis according to claim 4 further comprising a supporting stent, said supporting stent being located at said other end of said graft.

6. A prosthesis of claim 5 wherein said supporting stent being inside said graft.

7. A prosthesis according to claim 5 wherein the supporting stent being exterior to said graft between said graft and an aortic wall.

8. A prosthesis according to claim 5 wherein said supporting stent is self-expanding.

9. A prosthesis according to claim 5 wherein said supporting stent is balloon expandable.

10. A prosthesis according to claim 1 wherein said graft is made from polymeric material which is selected from the group consisting of polyester, polypropylene, polyethylene, polytetrafluoroethylene, expanded polytetrafluoroethylene, polyurethane and combinations thereof.

11. The prosthesis according to claim 1 wherein said stent is made from metallic material which is selected from the group consisting of stainless steel, platinum, gold, titanium and combinations thereof.

12. The prosthesis according to claim 1 wherein said stent is made from polymeric materials.

13. The prosthesis according to claim 1 wherein said stent is nitinol.

14. A stent/graft composite prosthesis comprising:
   an elongate self-expanding tubular stent, said stent having opposed stent ends and an open wall structure therebetween having an internal surface;
   an elongate compressible tubular graft having opposed graft ends; said graft being secured at one graft end thereof to said internal surface of said stent adjacent one stent end thereof to anchor said graft to an endoluminal wall, said graft wall extending unattached through said tubular stent to an unsupported graft end adjacent the other stent end, said unsupported graft end being unattached, said graft being attached only at said one end.

15. A prosthesis of claim 14 wherein said graft's unsupported end extends outwardly beyond said other stent end.

16. A prosthesis of claim 15 further including a supporting stent, said supporting stent being positioned adjacent said unsupported end of said graft.

17. A prosthesis of claim 16 wherein said supporting stent is positioned inwardly of said tubular graft.

18. A prosthesis of claim 16 wherein said supporting stent is positioned externally of said tubular graft.

19. A prosthesis according to claim 16 wherein said supporting stent is self-expanding.

20. A prosthesis according to claim 16 wherein said supporting stent is balloon expandable.

21. A prosthesis according to claim 14 wherein said graft is made from polymeric material which is selected from the group consisting of polyester, polypropylene, polyethylene, polytetrafluoroethylene, expanded polytetrafluoroethylene, polyurethane and combinations thereof.

22. The prosthesis according to claim 14 wherein said stent is made from metallic material which is selected from the group consisting of stainless steel, platinum, gold, titanium and combinations thereof.

23. The prosthesis according to claim 14 wherein said stent is made from polymeric materials.

24. The prosthesis according to claim 14 wherein said stent is nitinol.

25. An endoluminal self-expanding prosthesis, comprising:
 an elongate stent having a pair of spaced apart ends and an open tubular wall structure therebetween, said tubular wall structure having an internal surface defining a stent lumen;
 an elongate graft having opposed ends and a graft wall therebetween, one end of said graft being secured to said internal surface of said stent to anchor said graft to an endoluminal wall, said graft wall extending unattached from said one end through said stent lumen to another end of said graft, said other end of said graft being unattached, said graft being attached only at said one end; and
 a supporting stent, said supporting stent being located at said other end of said graft, said supporting stent being unattached to said other end of said graft.

* * * * *